United States Patent [19]
Jaster et al.

[11] Patent Number: 5,545,942
[45] Date of Patent: Aug. 13, 1996

[54] METHOD AND APPARATUS FOR DISSIPATING HEAT FROM A TRANSDUCER ELEMENT ARRAY OF AN ULTRASOUND PROBE

[75] Inventors: Heinz Jaster, Schenectady, N.Y.; Gregg W. Frey, East Wenatchee, Wash.

[73] Assignee: General Electric Company, Milwaukee, Wis.

[21] Appl. No.: 343,063

[22] Filed: Nov. 21, 1994

[51] Int. Cl.$^6$ .................................................. H01L 41/08
[52] U.S. Cl. ........................... 310/341; 310/334; 310/340; 310/346; 174/16.3
[58] Field of Search ..................................... 310/334–336, 310/341, 342, 344, 346, 340; 174/16.3, 52.2

[56] References Cited

U.S. PATENT DOCUMENTS

| | | | |
|---|---|---|---|
| 3,071,736 | 1/1963 | Vonbun et al. | 310/341 X |
| 4,553,059 | 11/1985 | Abe et al. | 310/341 X |
| 5,272,599 | 12/1993 | Koenen | 174/16.3 X |
| 5,309,321 | 5/1994 | Olla et al. | 174/16.3 X |
| 5,420,751 | 5/1995 | Burns | 174/16.3 X |
| 5,446,620 | 8/1995 | Burns | 174/16.3 X |

FOREIGN PATENT DOCUMENTS 0058384  2/1990  Japan ..................... 310/341

*Primary Examiner*—Mark O. Budd
*Attorney, Agent, or Firm*—Dennis M. Flaherty; John H. Pilarski

[57] ABSTRACT

A device for improving heat dissipation inside an ultrasound probe and reducing heat build-up near the transducer face. Heat conductors are placed around the periphery of the transducer package, but within the probe housing, so that heat can be drawn away from the transducer face and toward the rear/interior of the probe. The heat conductors act as conduits for draining away heat which builds up in the thermal potting material during pulsation of the piezoelectric transducer elements. The heat conductors are formed from metal foil having a heat conductivity greater than the heat conductivity of the thermal potting material which fills the spaces inside the probe housing and surrounds the transducer package. The preferred metal foil is aluminum.

14 Claims, 2 Drawing Sheets

METHOD AND APPARATUS FOR DISSIPATING HEAT FROM A TRANSDUCER ELEMENT ARRAY OF AN ULTRASOUND PROBE

FIELD OF THE INVENTION

This invention generally relates to probes used in ultrasonic imaging of the human anatomy. In particular, the invention relates to techniques for limiting the build-up of transducer-generated heat on the exterior of an ultrasound probe.

BACKGROUND OF THE INVENTION

A conventional ultrasonic probe comprises a transducer package which must be supported within the probe housing. As shown in FIG. 1, a conventional transducer package 2 comprises a linear array 4 of narrow transducer elements. Each transducer element is made of piezoelectric material. The piezoelectric material is typically lead zirconate titanate (PZT), polyvinylidene difluoride, or PZT ceramic/polymer composite.

The design and fabrication of individual transducer elements with desirable acoustic properties, e.g., high sensitivity, wide bandwidth, short impulse response, and wide field of view, is a well known art.

Typically, each transducer element has a metallic coating on opposing front and back faces to serve as electrodes. The metallic coating on the front face serves as the ground electrode. The ground electrodes of the transducer elements are all connected to a common ground. The metallic coating on the back face serves as the signal electrode. The signal electrodes of the transducer elements are connected to respective electrical conductors formed on a flexible printed circuit board (PCB) 6.

During operation, the signal and ground electrodes of the piezoelectric transducer elements are connected to an electrical source having an impedance $Z_s$. When a voltage waveform is developed across the electrodes, the material of the piezoelectric element compresses at a frequency corresponding to that of the applied voltage, thereby emitting an ultrasonic wave into the media to which the piezoelectric element is coupled. Conversely, when an ultrasonic wave impinges on the material of the piezoelectric element, the latter produces a corresponding voltage across its terminals and the associated electrical load component of the electrical source.

In conventional applications, each transducer element produces a burst of ultrasonic energy when energized by a pulsed waveform produced by a transmitter (not shown). The pulses are transmitted to the transducer elements via the flexible PCB 6. This ultrasonic energy is transmitted by the probe into the tissue of the object under study. The ultrasonic energy reflected back to transducer element array 4 from the object under study is converted to an electrical signal by each receiving transducer element and applied separately to a receiver (not shown).

The alternating release and absorption of acoustic energy during transmission and reception creates a thermal build-up in the probe due to acoustic losses being converted into heat. The amount of heat that can be allowed to build up on the exterior of an ultrasound probe must be within prescribed limits. Typically the limit is that the temperature on any outer surface of the probe cannot exceed 40° C. Most of the heat tends to build up immediately around the transducer elements, which are necessarily situated in the probe very close to the body of the patient being examined.

The transducer package 2 also comprises a mass of suitable acoustical damping material having high acoustic losses positioned at the back surface of the transducer element array 4. This backing layer 12 is coupled to the rear surface of the transducer elements to absorb ultrasonic waves that emerge from the back side of each element so that they will not be partially reflected and interfere with the ultrasonic waves propagating in the forward direction.

Typically, the front surface of each transducer element of array 4 is covered with a first acoustic impedance matching layer 8 shown in FIG. 1. The first matching layer 8 may consist of a glass material such as Pyrex® borosilicate glass. Typically, a second acoustic impedance matching layer is later bonded to the first acoustic impedance matching layer. The impedance matching layers transform the high acoustic impedance of the transducer elements to the low acoustic impedance of the human body and water, thereby improving the coupling with the medium in which the emitted ultrasonic waves will propagate.

The transducer element array, backing layer and first acoustic impedance matching layer are all bonded together in a stack-up arrangement, as seen in FIG. 1. During assembly of the ultrasonic probe, the transducer stack-up must be held securely within the probe housing (not shown in FIG. 1). Typically, this is accomplished by securing the transducer stack-up within a four-sided array case 14, i.e., a "box" having four side walls but no top or bottom walls, as shown in FIG. 2. The array case is made of electrically conductive material and provides a common ground for connection with the ground electrodes of the transducer elements. The transducer stack-up is inserted into a recess in the array case 14 until the bottom surface of the first acoustic impedance matching layer 8 is flush with the bottom edge of the array case. The transducer stack-up is conventionally bonded inside the array case using epoxy. Then a second acoustic impedance matching layer 10 is conventionally bonded to those flush bottom surfaces (see FIG. 2). Matching layer 10 may consist of a plastic material, such as Plexiglas® acrylic resin plastic.

During assembly of an ultrasonic probe incorporating the structure of FIG. 2, transducer package 2 must be secured within the probe housing (not shown). The interior volume of the probe housing surrounding the transducer package is filled with thermally conductive potting material, e.g., heat-conductive ceramic granules embedded in epoxy. The potting material stabilizes the construction and assists in dissipating heat, generated during pulsation of the transducer element array, away from the probe surface/transducer face toward the interior/rear of the probe.

SUMMARY OF THE INVENTION

The present invention is a device for improving heat dissipation inside an ultrasound probe and reducing heat build-up near the transducer face. In accordance with a preferred embodiment, aluminum foil heat conductors are placed around the periphery of the transducer package (but within the probe housing) so that heat can be drawn away from the transducer face and toward the rear/interior of the probe. Heat conductive, electrically nonconductive materials other than aluminum can be used provided that the material is compatible with the thermal potting material in contact therewith and can be easily fabricated into the desired shape.

The heat conductors in accordance with the invention act as conduits for draining heat from the thermal potting material which fills the spaces inside the probe housing. The heat which accumulates in the thermal potting material is the product of acoustic losses in the transducer element array. Thus, the heat conductors are effectively thermally coupled to the transducer element array. This arrangement increases the ability to dissipate heat away from the transducer package and thus away from the patient being examined.

Optionally, the heat conductors in accordance with the invention can be thermally coupled to the shielding braid of the coaxial cable of the probe. Connection to the shielding braid facilitates the transfer of even more heat away from the transducer element array.

DETAILED DESCRIPTION OF THE PREFERRED EMBODIMENTS

Figure 1:
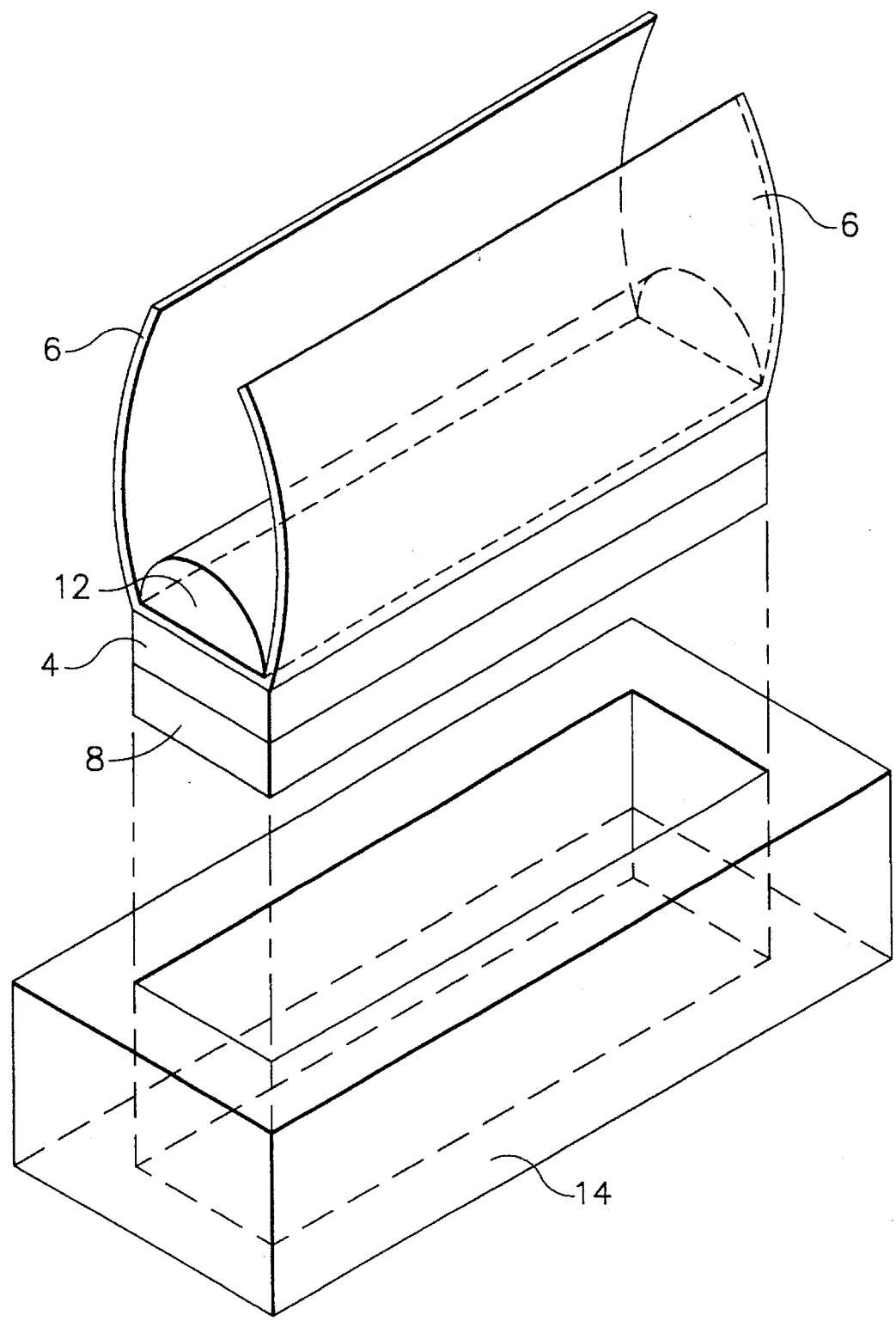
FIG. 1 is a schematic exploded view of parts of a conventional transducer package for use in an ultrasonic probe.
Figure 2:
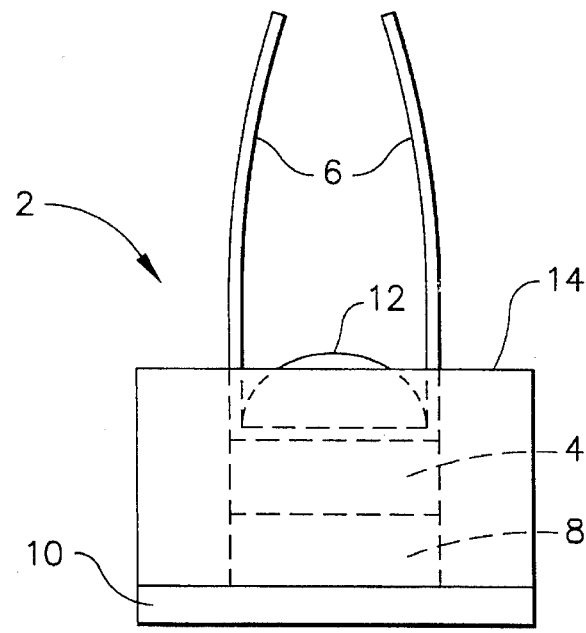
FIG. 2 is a schematic end view of a conventional transducer package showing the transducer stack-up installed inside the array case with an acoustic impedance matching layer bonded to the face of the assembly.
Figure 3:
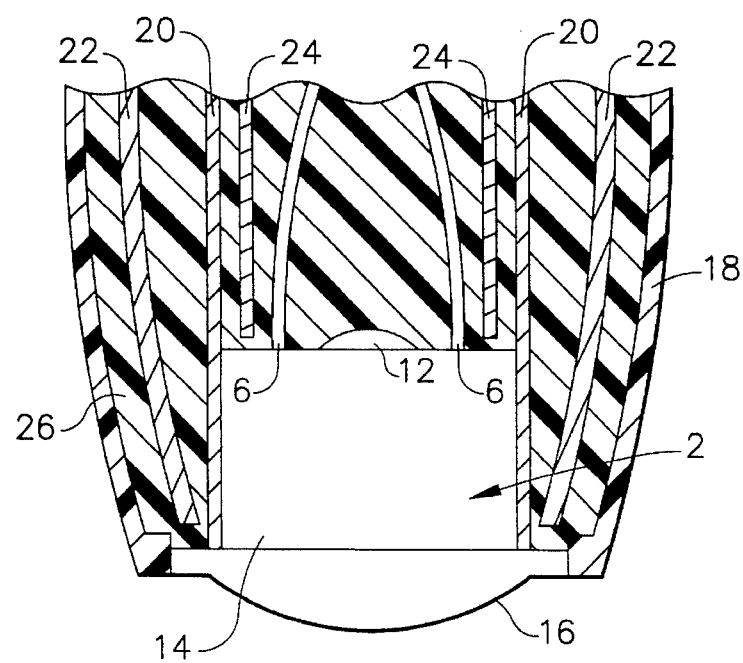
FIG. 3 is a schematic partly sectional view of the tip portion of an ultrasound probe incorporating means for dissipating heat away from the transducer element array in accordance with the preferred embodiment of the invention.

Referring to FIG. 3, an ultrasound probe in accordance with the preferred embodiment of the invention comprises a transducer package 2, the front face of which is seated in a corresponding recess formed in a cylindrical focusing lens 16. Focusing lens 16 may be made of silicone rubber, for example. This layer of silicone rubber serves three purposes: (1) acoustic focusing (due to its lens-shaped cross section and its low acoustic velocity material properties); (2) providing a chemical barrier to protect the transducer elements from attack by gels, body fluids, cleaning agents, etc.; and (3) providing an electrical barrier to protect the patient from the electrically active transducer elements.

The transducer package 2 and focusing lens 16 are mounted inside the ultrasound probe by adhesively bonding the perimeter of lens 16 in an aperture of corresponding shape formed in the tip of a probe housing 18 and then filling the probe interior with conventional thermal potting material 26. The cured potting material surrounds the transducer package 2 and absorbs heat generated due to acoustic losses in the transducer elements. The thermal potting material may consist, for example, of heat-conductive ceramic granules embedded in cured epoxy.

In accordance with conventional practice, the perimeter of the transducer package may be surrounded with a sheet of electrically conductive foil to form an electrical shield 20. The conventional shield is made of tin-plated copper foil, one side of which is coated with conductive adhesive. The adhesive-coated side of the shield can be adhered to the outer peripheral surfaces of the array case 14 as the foil is wrapped therearound. The edges of the foil are overlapped, with the adhesive-coated side of one edge pressed against and adhered to the non-adhesive-coated side of the other edge. The gap between the overlapping edges is thus sealed by the conductive adhesive. The resulting enclosure shields against radiofrequency interference and stray electrical fields.

In accordance with one preferred embodiment of the present invention, a pair of outer heat sinks or conductors 22 are embedded in the thermal potting material 26, as shown in FIG. 3. Preferably, the outer heat conductors 22 are located between the portions of the electrical shield 20 which cover the long sides of the transducer array case 14 and the opposing portions of the probe housing 18. Each outer heat conductor 22 comprises a sheet made of material having excellent heat conductivity. In the preferred embodiment, each outer heat conductor 22 comprises a sheet of aluminum foil. Each foil sheet has a distal end which lies in proximity to the periphery of the transducer element array. From the distal end, the foil sheets of heat conductors 22 extend toward the rear of the probe. These aluminum foil heat conductors 22 are placed around the periphery of the transducer package 2, but within the probe housing 18 so that heat can be drawn away from the transducer face and toward the rear and interior of the probe. In particular, the outer heat conductors 22 act as conduits for draining away heat which builds up in the thermal potting material 26 surrounding the periphery of the array case 14. This heat build-up is due to acoustic losses in the transducer element array, which losses are converted into heat by the piezoelectric material. This heat is conducted from the piezoelectric material to the thermal potting material 26 via the walls of the array case 14 and the electrical shield foil 20. In accordance with the present invention, the heat conductors are made of a material having a thermal conductivity greater than the thermal conductivity of the thermal potting material 26. Therefore, heat conductors 22 dissipate the excess heat which builds up in the thermal potting material. Optionally, the heat conductors 22 can be thermally coupled to the shielding braid of the coaxial cable (not shown) of the probe. Connection to the shielding braid facilitates the transfer of even more heat away from the transducer element array.

In accordance with a further feature of the preferred embodiment, a pair of inner heat sinks or conductors 24 are embedded in the thermal potting material 26, as shown in FIG. 3. Preferably, the inner heat conductors 24 are located between the flexible PCB 6 and electrical shield 20. Each inner heat conductor 24 comprises a sheet made of the same material used for the heat conductors 22, i.e., a material having excellent heat conductivity, such as aluminum foil. Each foil sheet has a distal end which lies in proximity to the Upper edge of a side wall of array case 14. From the distal end, the foil sheets of heat conductors 24 extend toward the rear of the probe. These aluminum foil heat conductors 24 draw additional heat away from the transducer face and toward the rear and interior of the probe.

Although the disclosed preferred embodiment has two inner heat conductors and two outer heat conductors, it will be apparent to persons skilled in the design of ultrasonic probes after reading this disclosure that other configurations can be used to dissipate heat from the transducer element array. For example, a single outer heat conductor in the form of an aluminum foil curtain laterally surrounding the transducer package could be used in place of two separate heat conductors. The edges of the curtain, although preferably in proximity to each other, need not be joined. Similarly, the two inner heat conductors could be replaced by a single aluminum foil curtain extending around the flexible PCB. As a further alternative, each sheet of aluminum foil can be replaced by a multiplicity of strips of aluminum foil, each strip having a distal end in proximity to the transducer package and extending from the distal end toward the rear of the probe. Thus, the number of separate outer heat conductors can be greater than two. Likewise the number of separate inner heat conductors can be greater than two.

Furthermore, the heat conductors of the present invention need not be made of aluminum foil, although the latter is preferred. Heat conductive materials other than aluminum can be used provided that the material is compatible with the thermal potting material in contact therewith and can be easily fabricated into the desired shape. Suitable alternative exemplary materials include copper, silver, gold, tin, iron and lead.

The foregoing preferred embodiment has been disclosed for the purpose of illustration. Variations and modifications which do not depart from the broad concept of the invention will be readily apparent to those skilled in the design of ultrasonic probes. All such variations and modifications are intended to be encompassed by the claims set forth hereinafter.

We claim:

1. An ultrasonic probe comprising:

a probe housing having an internal volume and a tip with an aperture formed therein, said aperture being in communication with said internal volume;

a plurality of transducer elements made of piezoelectric material and arranged in a planar array, said planar array being located in said internal volume of said probe housing and having a predetermined orientation relative to said aperture formed in said tip of said probe housing, each transducer element having an electrode formed on the piezoelectric material thereof;

means for securing said planar array relative to said probe housing, said securing means comprising thermally conductive potting material which fills a portion of said internal volume of said of said probe housing, said potting material having a heat conductivity in a predetermined range; and heat conducting means embedded in said potting material and extending from a first location to a second location, said first location being a first distance away from a closest portion of said planar array and said second location being a second distance away from said closest portion of said planar array, said second distance being greater than said first distance, wherein said heat conducting means are made of a material having a heat conductivity greater than the heat conductivity of said potting material, further comprising a flexible electrical circuit means electrically connected to said electrodes of said transducer elements, and a coaxial cable electrically connected to said flexible electrical circuit means, said coaxial cable incorporating shielding braid, wherein said heat conducting means are thermally coupled to said shielding braid of said coaxial cable.

2. The ultrasonic probe as defined in claim 1, wherein said heat conducting means comprise aluminum foil.

3. The ultrasonic probe as defined in claim 1, wherein said material of said heat conducting means comprises a metal.

4. The ultrasonic probe as defined in claim 1, wherein said securing means further comprises an array case having a recess in which said planar array of transducer elements is secured along a periphery thereof, and said heat conducting means comprise heat conductive metal foil extending into a portion of said internal volume of said probe housing located between said array case and said probe housing.

5. The ultrasonic probe as defined in claim 4, further comprising an electrical shield secured to outer peripheral surfaces of said array case, wherein said heat conducting means further comprise heat conductive metal foil extending into a portion of said internal volume of said probe housing located between said flexible electrical circuit means and said electrical shield.

6. The ultrasonic probe as defined in claim 1, wherein said heat conducting means extend away from a location near said tip of said probe housing and toward a rear end of said probe.

7. An ultrasonic probe comprising:

a probe housing having an internal volume and a tip with an aperture formed therein, said aperture being in communication with said internal volume;

a plurality of transducer elements made of piezoelectric material and arranged in a planar array, said planar array being located in said internal volume of said probe housing and having a predetermined orientation relative to said aperture formed in said tip of said probe housing, each transducer element having an electrode formed on the piezoelectric material thereof; and heat conducting means thermally coupled to said transducer elements for drawing heat away therefrom, wherein said heat conducting means comprise a first metal foil, further comprising a flexible electrical circuit means electrically connected to said electrodes of said transducer elements, and a coaxial cable electrically connected to said flexible electrical Circuit means, said coaxial cable incorporating shielding braid, wherein said heat conducting means are thermally coupled to said shielding braid of said coaxial cable.

8. The ultrasonic probe as defined in claim 7, wherein said first metal foil is made of a pure metal having good thermal conductivity, such as aluminum, copper, silver and gold.

9. The ultrasonic probe as defined in claim 7, further comprising an electrical shield secured to outer peripheral surfaces of said array case, wherein said heat conducting means further comprise a second metal foil extending into a portion of said internal volume of said probe housing located between said flexible electrical circuit means and said electrical shield.

10. The ultrasonic probe as defined in claim 9, further comprising flexible electrical circuit means electrically connected to said transducer elements and an electrical shield secured to outer peripheral surfaces of said array case, wherein said heat conducting means further comprise a second metal foil extending into a portion of said internal volume of said probe housing located between said flexible electrical circuit means and said electrical shield.

11. The ultrasonic probe as defined in claim 10, wherein said first and second metal foils are made of a pure metal having good thermal conductivity, such as aluminum, copper, silver and gold.

12. The ultrasonic probe as defined in claim 7, further comprising thermal potting material having a heat conductivity in a predetermined range, wherein said thermal potting material fills portions of said internal volume of said probe housing, said first metal foil being embedded in said thermal potting material and having a heat conductivity greater than said heat conductivity of said thermal potting material.

13. The ultrasonic probe as defined in claim 7, further comprising:

an array case having a recess in which said planar array of transducer elements is secured along a periphery thereof; and an electrical shield secured to outer peripheral surfaces of said array case, wherein said first metal foil extends into a portion of said internal volume of said probe housing located between said flexible electrical circuit means and said electrical shield.

14. The ultrasonic probe as defined in claim 13, wherein said first metal foil is made of a pure metal having good thermal conductivity, such as aluminum, copper, silver and gold.

* * * * *